United States Patent
Ragusa et al.

(10) Patent No.: US 10,228,310 B2
(45) Date of Patent: Mar. 12, 2019

(54) FLOW THROUGH FLUID SAMPLING SYSTEM AND METHOD OF USING SAME

(71) Applicant: Haemonetics Corporation, Braintree, MA (US)

(72) Inventors: Michael Ragusa, Hingham, MA (US); Matthew J. Murphy, Marshfield, MA (US)

(73) Assignee: Haemonetics Corporation, Braintree, MA (US)

( * ) Notice: Subject to any disclaimer, the term of this patent is extended or adjusted under 35 U.S.C. 154(b) by 65 days.

(21) Appl. No.: 15/110,879

(22) PCT Filed: Jan. 12, 2015

(86) PCT No.: PCT/US2015/011003
§ 371 (c)(1),
(2) Date: Jul. 11, 2016

(87) PCT Pub. No.: WO2015/106191
PCT Pub. Date: Jul. 16, 2015

(65) Prior Publication Data
US 2016/0334307 A1    Nov. 17, 2016

Related U.S. Application Data

(60) Provisional application No. 61/926,914, filed on Jan. 13, 2014.

(51) Int. Cl.
| | |
|---|---|
| *G01N 1/20* | (2006.01) |
| *A61B 5/15* | (2006.01) |
| *B01L 3/00* | (2006.01) |
| *G01N 1/38* | (2006.01) |
| *A61B 10/00* | (2006.01) |

(Continued)

(52) U.S. Cl.
CPC ..... *G01N 1/2035* (2013.01); *A61B 5/150992* (2013.01); *A61B 10/0045* (2013.01);
(Continued)

(58) Field of Classification Search
CPC .......... G01N 1/2035; G01N 1/20; G01N 1/10; G01N 1/02; A61B 5/150992; A61B 5/15; A61B 5/00; A61B 10/0045; B01L 3/502; B01L 3/50; B01L 3/00
(Continued)

(56) References Cited

U.S. PATENT DOCUMENTS 4,134,512 A * 1/1979 Nugent .............. A61B 5/15003
215/247
4,744,785 A * 5/1988 Rosenthal ........... A61M 1/0001
604/319

(Continued)

OTHER PUBLICATIONS

Blaine R. Copenheaver, *Authorized officer* United States Patent and Trademark Office (ISA), International Search Report—Application No. PCT/US2015/011003, dated Mar. 18, 2015, 11 pages.

(Continued)

*Primary Examiner* — Christine T Mui
(74) *Attorney, Agent, or Firm* — McCarter & English, LLP; Jonathan C. Lovely (57) ABSTRACT

A flow through fluid sampling system includes a sample tube and a cap. The sample tube is configured to collect a sample of a fluid and has an open top. The cap is configured to be secured to the sample tube to close the open top. The cap includes an inflow port configured to allow fluid to enter the fluid sample tube, an outflow port configured to allow fluid to leave the sample tube.

22 Claims, 6 Drawing Sheets

(51) Int. Cl.
*G01N 33/49* (2006.01)
*G01N 1/10* (2006.01)

(52) U.S. Cl.
CPC ........... *B01L 3/502* (2013.01); *B01L 3/50825* (2013.01); *G01N 1/38* (2013.01); *G01N 33/49* (2013.01); *B01L 2300/042* (2013.01); *B01L 2300/046* (2013.01); *B01L 2300/047* (2013.01); *B01L 2300/048* (2013.01); *B01L 2300/0681* (2013.01); *B01L 2300/0851* (2013.01); *G01N 33/491* (2013.01); *G01N 2001/2071* (2013.01)

(58) Field of Classification Search
USPC ......... 436/177; 210/645, 780; 600/366, 309, 600/573, 300; 604/6.09, 5.01, 4.01, 403, 604/409, 408
See application file for complete search history.

(56) References Cited

U.S. PATENT DOCUMENTS

| | | | | |
|---|---|---|---|---|
| 5,132,026 A | * | 7/1992 | Baluyot | A61J 1/05 210/257.1 |
| 5,363,860 A | | 11/1994 | Nakao et al. | |
| 6,152,902 A | * | 11/2000 | Christian | A61M 1/0001 604/319 |
| 2011/0139276 A1 | * | 6/2011 | Kashmiran | A61B 5/155 137/561 R |

OTHER PUBLICATIONS

Nina Jansson Godoy, Examiner European Patent Office, Supplementary European Search Report—Application No. EP 15735431.7, dated Aug. 8, 2017, 8 pages.

* cited by examiner

FLOW THROUGH FLUID SAMPLING SYSTEM AND METHOD OF USING SAME

PRIORITY

This patent application claims priority from U.S. Provisional Patent Application No. 61/926,914, filed Jan. 13, 2014, entitled, "Flow Through Sampling System," and naming Michael Ragusa, and Matt Murphy as inventors, the disclosure of which is incorporated herein, in its entirety, by reference.

TECHNICAL FIELD

The present invention relates to sampling systems, and more particularly to flow through sampling systems.

BACKGROUND ART

Apheresis is a procedure in which an individual blood component can be separated and collected from whole blood withdrawn from a subject. Typically, whole blood is withdrawn through a needle inserted into the subject's arm and transferred into a cell separator, such as a centrifugal bowl. Once the whole blood is separated into its various components (e.g., plasma, red blood cells, and platelets), one or more of the components can be collected from the centrifugal bowl. The remaining components can be returned to the subject along with a compensation fluid to make up for the volume of the removed component.

During the apheresis procedure (e.g., during plasmapheresis), a sample of the collected components (e.g., plasma) may be taken for later analysis and testing. Current sampling systems utilize an injection site with a stopple. However, samples collected in this manner must be completed off-line and after the collected product has been transferred to a laboratory. This process is also labor intensive due to the number of manual manipulations required to take the sample.

SUMMARY OF THE EMBODIMENTS

In a first embodiment of the invention there is provided a flow through fluid sampling system that includes a sample tube and a cap. The sample tube may be configured to collect a sample of a fluid and may have an open top. The cap is configured to be secured to the sample tube to close the open top, and may include an inflow port and an outflow port. The inflow port is configured to allow fluid to enter the fluid sample tube, and the outflow port is configured to allow fluid to leave the sample tube. In some embodiments, the inflow port may be configured to be fluidly connected to a blood separation device (e.g., the inlet and/or the outlet of the separation device) of a plasmapheresis system, and the outflow port may be configured to be fluidly connected to a plasma storage bottle.

The system may also include an occluder located within the cap. The occluder may impinge the flow of fluid from the inflow port, thereby reducing mixing within the sample tube. Additionally or alternatively, the system may include a chamber within the cap. The chamber may have a bottom wall that includes a flow path extending through it. The chamber may be located between the inflow port and the sample tube, and the sample tube may be in fluid communication with the chamber via the flow path. The system may have a vent channel that extends through the cap, and is configured to allow air from the sample tube to vent through the vent channel. In some embodiments, the vent channel may include a bacteriostatic filter that is configured to stop air flow through the bacteriostatic filter when wet.

In accordance with additional embodiments, a method for collecting a sample of fluid includes connecting a flow through fluid sampling system to a line through which a fluid flows. The fluid sampling system may include a sample tube that is configured to collect a sample of a fluid and has an open top, and a cap configured to be secured to the sample tube to close the open top. The cap may include an inflow port configured to allow fluid to enter the fluid sample tube from the line, and an outflow port configured to allow fluid to exit the sample tube and re-enter the line. The method may also include flowing fluid through the line such that at least a portion of the fluid flowing through the line enters the sample tube through the inflow port.

As the fluid enters the sample tube it may mix with fluid already within the tube. Additionally, at least a portion of the fluid entering the sample tube may exit the sample tube through the outflow port. In some embodiments, the method may also include fluidly connecting the inflow port to a blood separation device (e.g., an outlet of the blood separation device) of a plasmapheresis system, and fluidly connecting the outflow port to a plasma storage bottle.

The cap may also include an occluder that impinges the flow of fluid from the inflow port and reduces mixing within the sample tube. Additionally or alternatively, the fluid sampling system may include a chamber within the cap. The chamber may have a bottom wall and may be located between the inflow port and the sample tube. The bottom wall may include a flow path extending through it, and the chamber and the sample tube may be in fluid communication via the flow path.

In further embodiments, the fluid sampling port may include a vent channel that extends through the cap, and air from the sample tube may be vented through the vent channel as fluid enters the sample tube. The vent channel may include a bacteriostatic filter that is configured to stop air flow through the bacteriostatic filter when wet.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

In illustrative embodiments, a flow through sampling system may be used in conjunction with a blood processing device to collect a sample of one or more blood components during an apheresis procedure. For example, the flow through sampling system may be located on tubing fluidly connecting the blood processing device (e.g., a centrifuge bowl within the blood processing device) and a blood component storage container such that the sample is collected within the sampling system as the blood component (e.g., plasma) is transferred from the blood processing device to the storage container. Details of illustrative embodiments are discussed below.

Figure 1:
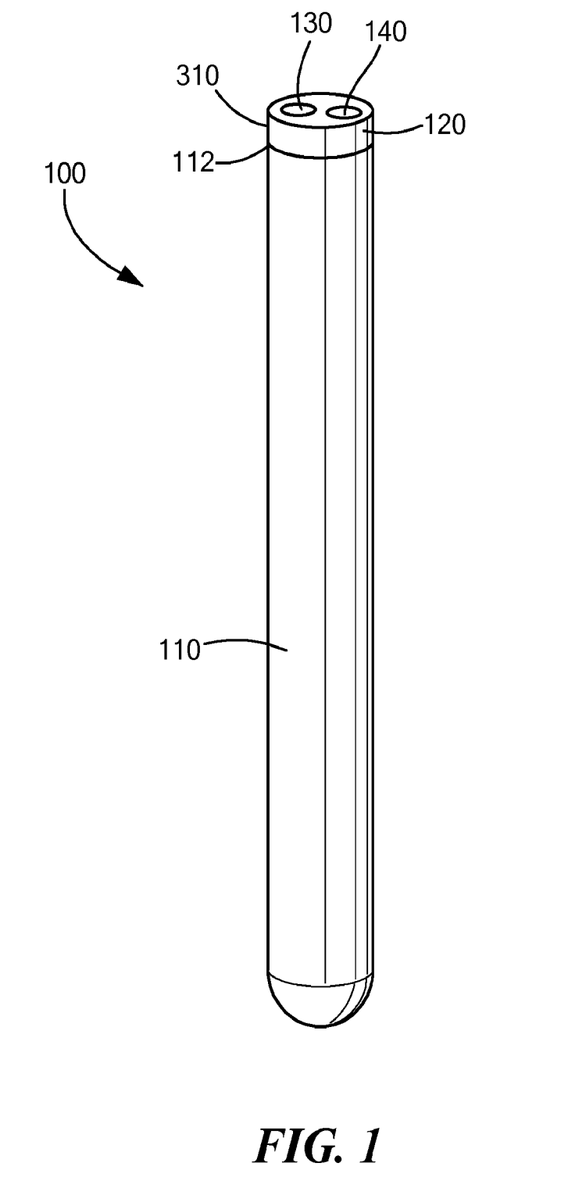
FIG. 1 schematically shows a flow through sampling system in accordance with various embodiments of the present invention.

FIG. 1 shows a flow though sampling system 100 in accordance with some embodiments of the present invention. The sampling system 100 may include a sample tube 110 in which the sample may be collected and a cap 120. Although any number of sample tubes 110 may be used, in some embodiments, the sample tube 110 may be a standard configuration test tube having an open top/end 112. However, in further embodiments (discussed in greater detail below), the sample tube may be a tube/collection chamber having an adapter to which a vacuum sealed sample tube/container (e.g., a VACUTAINER™) may be connected.

The cap 120 may fit onto the sample tube 110 to close the open end 112 of the sample tube 110. For example, the cap may fit over and/or within the open end 112 of the sample tube 110 and may cover/close the open end 112 during sample collection. To facilitate flow into the sample system 100 (and the sample tube 110), the cap 120 may have an inflow port 130. Similarly, to facilitate flow out of the sample system 100, the cap also has an outflow port 140.

Figure 2:
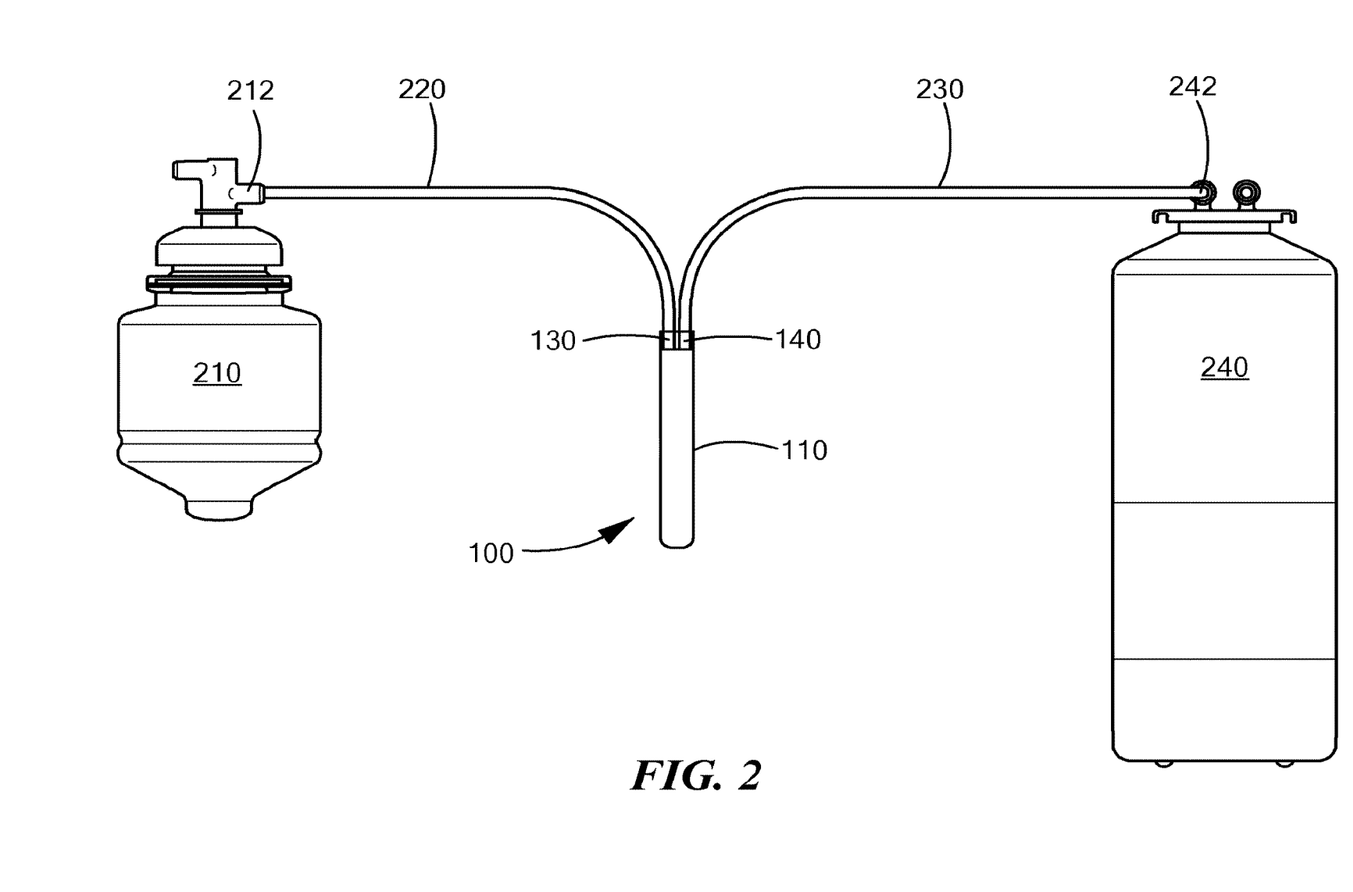
FIG. 2 schematically shows the flow through sampling system of FIG. 1 connected to an apheresis system, in accordance with some embodiments of the present invention.

As shown in FIG. 2 and as discussed above, some embodiments of the sampling system 100 may be connected to a blood collection/processing system (e.g., an apheresis system) and used to collect a sample of one or more of the blood components that are being collected/processed by the blood processing and collection system. To that end, the sampling system 100 may be placed in-line between the blood component separation device 210 of the blood collection/processing system, and a blood component collection container 240 (e.g., a plasma container). For example, the inflow port 130 of the sampling system 100 may be fluidly connected (e.g., via tubing 220) to a port (e.g., the outlet 212) on the blood component separation device 210 (e.g., a centrifuge bowl), and the outflow port 140 may be fluidly connected to a port (e.g., the inlet 242) on the storage container 240.

In such embodiments, after whole blood is separated into its individual components (e.g., plasma, platelets, red blood cells, white blood cells, etc.) and as one or more of the components (e.g., plasma) is being transferred to the collection container 240, the fluid to be sampled will pass through the line 220 connecting the outlet 212 of the separation device and the inflow port 120 of the sampling system 100, and into the sample tube 110 via the inflow port 120. Once in the sample tube 110, the fluid will mix with any fluid already contained within the sample tube 110 (e.g., the fluid/plasma already collected within the sample tube 110), and a portion of the fluid will exit the sampling system 100 via the outflow port 140, flow through the line 230 connecting the outflow port 140 and the inlet 242 on the collection container 240, and into the collection container 240. It is important to note that the fluid exiting the sample tube 110 via the outflow port 140 may include a portion of the mixed fluid within the tube 110, a portion of the new fluid entering the tube 110 via the inflow port 130, or a combination of both.

By placing the sampling system 100 in-line as described above, various embodiments of the sampling system 100 provide numerous advantages. For example, various embodiments of the sampling system 100 can collect a relatively small volume percentage of the fluid as it passes through (e.g. ~1-3%). This, in turn, allows the sampling system 100 to collect the fluid in a metered manner over a period of time. Furthermore, because the fluid is collected in a metered manner over a period of time and because the fluid entering the sampling system 100 mixes with fluid already collected, the final constitution of the sample is similar/identical to a homogenous sample of the large fluid volume (e.g., the larger volume of fluid/plasma being collected within the collection container 240).

Figure 3:
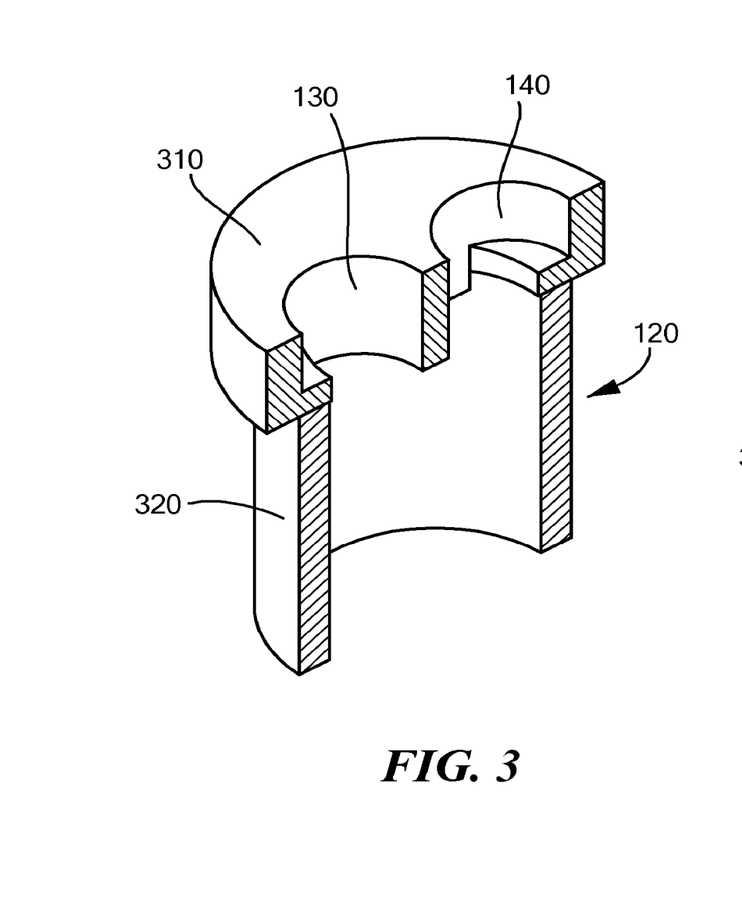
FIG. 3 schematically shows a first embodiment of a cap of the flow through sampling system, in accordance with some embodiments of the present invention.

As mentioned above, the cap 120 connects to the open end 112 of the sample tube 110. To that end, as best shown in FIG. 3, the cap 120 may have a proximal portion 310 and a distally extending portion 320 that extends downward (distally) from the proximal portion 310. In some embodiments, the proximal portion 310 may have a larger diameter/outer dimension than that of the distally extending portion 320 and may rest on the proximal face of the open end 112 of the sample tube 110 such that is located outside of the sample tube 110 (e.g., the proximal portion sits on top of the sample tube 110, as shown in FIG. 1). In such embodiments, the distally extending portion 320 may have an outer diameter/dimension that is slightly smaller than the inner diameter/dimension of the sample tube 110, and may extend into the sample tube 110.

It is important to note that, although the above cap 120 is described as having a distally extending portion 320 with a diameter/outer dimension that is smaller than that of the proximal portion 310 and smaller than the inner diameter/dimension of the tube 110 (e.g., such that it fits within the tube 110), other embodiments may have different configurations. For example, in some embodiments, the distally extending portion 320 may have an inner diameter/dimension that is larger the outer diameter/dimension of the sample tube 110. In such embodiments, the distally extending portion 320 may extend over the open end 112 of the sample tube 110.

As fluid enters the sampling system 100, the cap 120 shown in FIG. 3 allows the incoming fluid to flow directly into the sample tube 110, readily mix with the fluid within the tube 110, and then flow out of the outflow port 140. It is important to note that, because the incoming fluid flows directly into the sample tube 110 (e.g., there is no obstruction) and readily mixes with the fluid in the tube, at higher flow rates, the incoming fluid may fully flush/wash out the sample tube 110. For example, in some embodiments, a fluid volume of approximate 30 ml flowing at 90 ml/min will fully flush/wash out the sample tube 110. Therefore, such cap configurations may be particularly useful to collect a representative sample if the volume pumped is very small and/or has a low flow rate. Alternatively, the cap configuration shown in FIG. 3 may be used in applications having a larger pumped volume (e.g., the volume of fluid being transferred to the blood component collection container 240), if the user is seeking to collect the last amount of fluid to be pumped through (e.g., the end of the plasma being transferred from the separation device 210 to the storage container 240).

Figure 4:
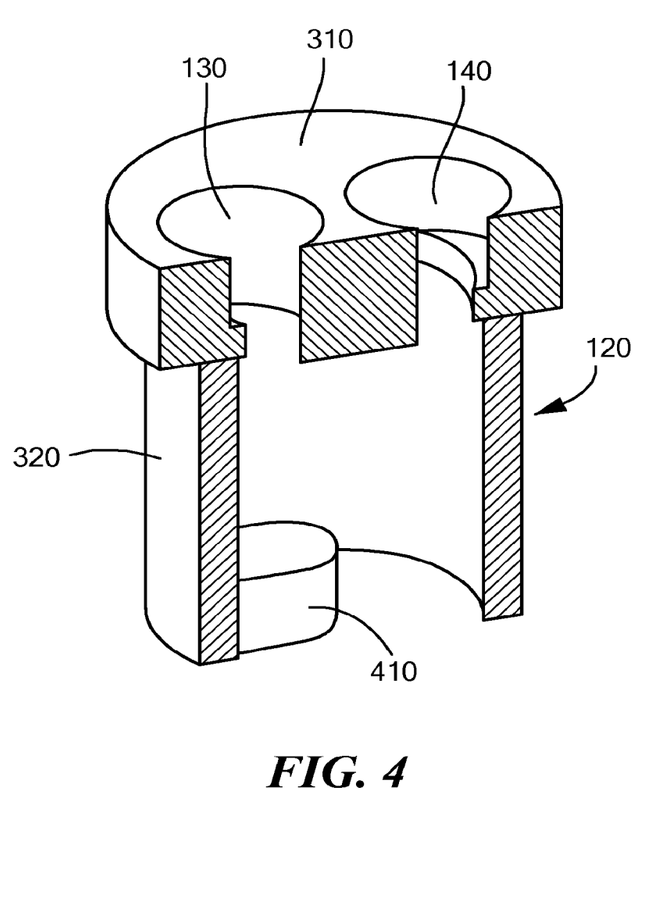
FIG. 4 schematically shows an alternative embodiment of a cap for the flow through sampling system, in accordance with additional embodiments of the present invention.

It should also be noted that, although the cap 100 described above and shown in FIG. 3 allows the fluid entering the sample tube 100 to readily mix with the fluid within the sample tube 100, in some applications, it may be beneficial to reduce and/or alter the level of mixing. To that end, some embodiments may include features within the cap 120 that alter the fluid mixing within the sample tube 110. For example, as shown in FIG. 4, the cap 120 may include an occluder 410 located on and extending inwardly from the distally extending portion 320 of the cap 120. Such features allow the level of mixing to be tailored based upon the application, fluid volume, and/or flow rate such that the fluid is metered in at a ratio that ensures the final sample collected within the tube 110 is representative of the entire volume of fluid collected within the storage container 240.

In embodiments having an occluder 410, as the fluid flows into the inflow port 130, the occluder 410 will impinge/obstruct the flow of fluid from the inflow port 130 into the tube 110. This, in turn, will reduce the level of mixing within the tube 100. With the addition of the occluder 410, the amount of pumped volume required to fully change over the contents of the sample tube 110 (e.g., to fully flush/wash out the sample tube 110) increases from approximately 30 ml (for embodiments not having an occluder 410, discussed above) to approximately 300 ml. The reduction in mixing and/or the increase in the volume required to fully change over the contents of the tube 110, in turn, results in a sample that is more representative of the entire fluid volume passing through the sampling system 100.

Figure 5:
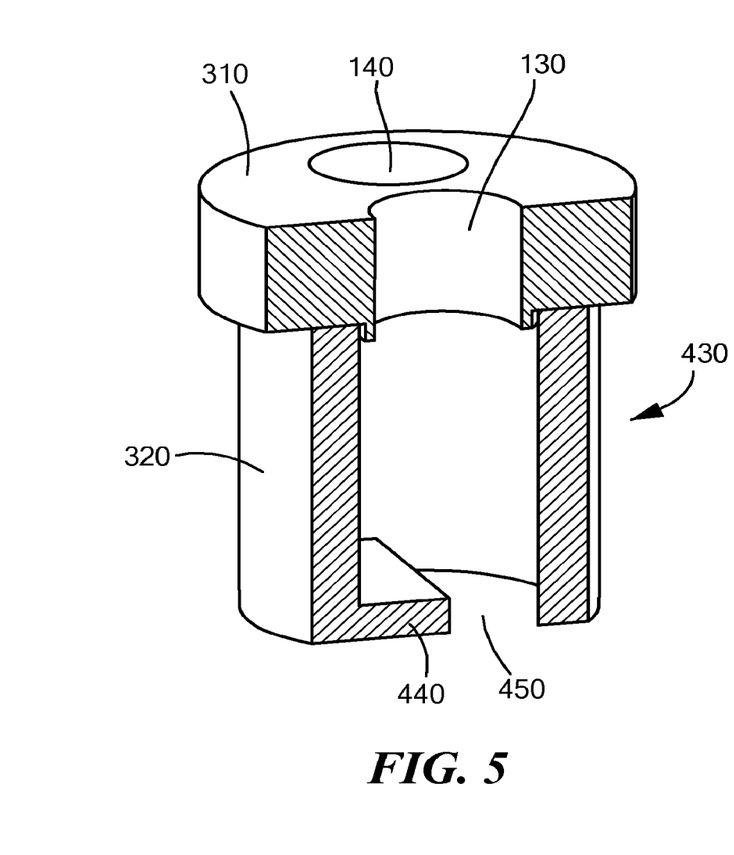
FIG. 5 schematically shows a further embodiment of a cap for the flow through sampling system, in accordance with additional embodiments of the present invention.

Although FIG. 4 shows a cap 100 having an occluder 410 with a semi-circular shape, some embodiments may have occluders 410 with different shapes, sizes and configurations. For example, as shown in FIG. 5, some embodiments may have an occluder 440 that is essentially a wall that extends outward from the bottom of the distally extending portion 320 of the cap 430 and covers a portion of the bottom opening 450 of the cap 430. By altering the size, shape, and configuration of the occluder 440, the amount of mixing can similarly, be altered.

Figure 6:
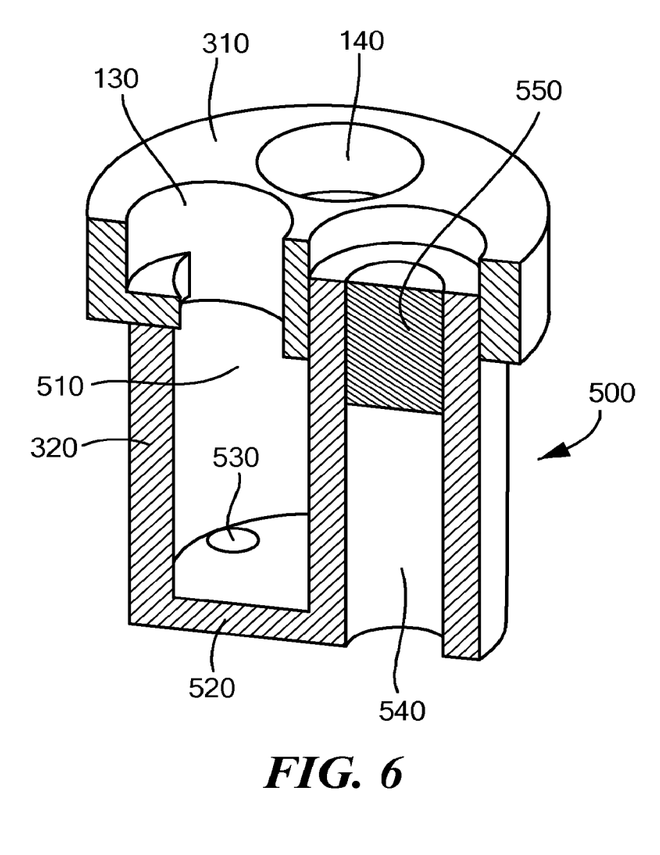
FIG. 6 schematically shows an additional alternative embodiment of a cap for the flow through sampling system, in accordance with additional embodiments of the present invention.

FIG. 6 shows an alternative embodiment of a cap 500 that may be used with the sampling system 100. Like the caps shown in FIGS. 4 and 5, the cap 500 shown in FIG. 6 can similarly have features that alter/minimize the mixing within the sample tube 110. For example, the cap 500 can have a chamber 510 (e.g., an antechamber) that is defined by the distally extending portion 320 of the cap 500 and a bottom wall 520. The inflow port 130 and the outflow port 140 are in fluid communication with the chamber 510 such that fluid may enter the chamber 510 through the inflow port 130 and exit the chamber 510 (e.g., to proceed onto the storage container 240) via the outflow port 140. To facilitate fluid communication between the chamber 510 and the sample tube 110, the bottom wall 520 has a flow path 530 (e.g., a hole) extending through it. As fluid enters the sampling system 100, the positive pressure created by pumping fluid from the separation device 210 to the storage container 240 will cause the fluid to gradually drip from the chamber 510 and into the sample tube 110.

As the fluid drips into the sample tube 110, air may be vented from the sample tube 110 via a vent channel 540 within the cap 500. The vent channel 540 may extend through the cap 500 and may include a bacteriostatic filter 550 that blocks one end of the vent channel 540. In some embodiments, the bacteriostatic filter 550 may be hydrophobic and/or designed to stop flow when it becomes wet. In such embodiments, when the sample tube 110 is full, the fluid within the sample tube 110 will contact and wet the filter 550. This, in turn, will prevent additional fluid from entering the sample tube 110 (e.g., because air/fluid within the sample tube 110 will no longer be able to exit the tube 110 via the vent channel 540), and will allow for only a small amount of mixing through the flow path 530 when the sample container 110 is full.

It is important to note that in embodiments containing the chamber 510 and the bacteriostatic filter 550, the fill rate of the sample tube 110 can be controlled by the size of the flow path 530 and/or the porosity of the filter 550. Therefore, if a quicker fill rate is desired, the diameter of the flow path 530 and/or the porosity of the filter 550 may be increased. Conversely, if a slower fill rate is desired, the diameter of the flow path 530 and/or the porosity of the filter 550 may be decreased. Similarly, because the size of the flow path impacts the amount of mixing, the diameter of the flow path 530 can be adjusted to alter the amount of mixing (e.g., the diameter may be increased to increase mixing or decreased to decrease mixing).

Figure 7:
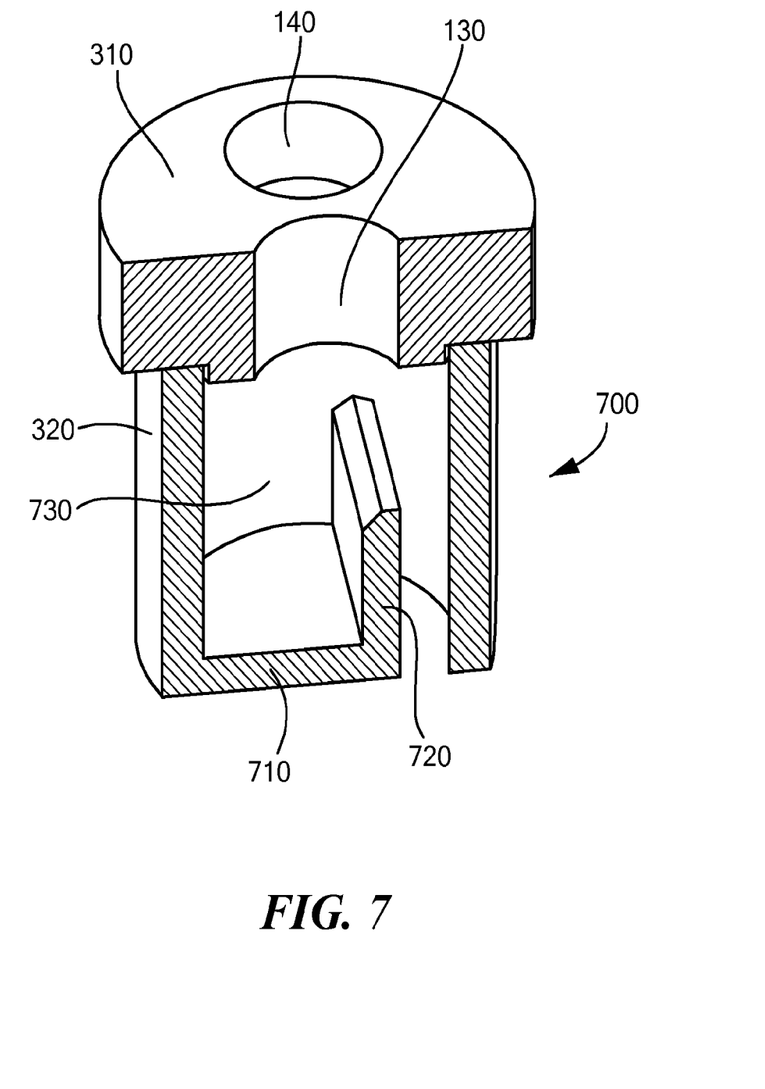
FIG. 7 schematically shows a fourth alternative embodiment of a cap for the flow through sampling system, in accordance with additional embodiments of the present invention.

FIG. 7 shows a further alternative embodiment of a cap 700 with additional features that alter the mixing within the sample tube 110. For example, in some embodiments, the cap 700 can include a horizontal wall 710 extending inwardly from the distally extending portion 320 of the cap 700 and a vertical wall 720 that extends proximally from the end of the horizontal wall 710 (e.g., toward the proximal portion 310 of the cap 700). In such embodiments, the horizontal wall 710 and the vertical wall 720 combine to form a chamber 730 within the cap 700 in which the fluid collects upon passing through the inflow port 130. For example, the fluid entering the sampling system 100 must flow into the cap 700 and chamber 730, where it will mix with the fluid in the chamber 730. As the chamber 730 fills, the fluid within the chamber 730 will flow over the vertical wall 720 and into the sample tube 110. This, in turn, will alter the mixing within the sampling system 100, because the fluid will first enter the chamber 730 prior to entering the sample tube 110.

It is important to note that, by modifying the level of mixing that occurs within the sample tube 110, various embodiments of the present invention are able to obtain a sample that is representative of the entire fluid volume being transferred from the separation device 210 and collected within the collection container 240. For example, in a plasma separation application, various embodiment of the present application are able to collect a plasma sample that is representative of the entire volume of plasma that is collected within the collection container 240. Furthermore, the level of mixing may be tailored to essentially meter in "new" fluid at a ratio that will ensure the sample collected within the tube is representative of the entire volume at the end of the process.

Although the above described embodiments are used to collect fluid as they are passing through a line (e.g., as they are being transferred from the blood separation device 210 and the plasma container 240), other embodiments of the present invention can be used to collect the sample after the plasma has been transferred to the plasma container 240. In such embodiments, the sampling system 100 may utilize a cap 120 similar to that shown in FIG. 1. Additionally, instead of standard a sample tube 110, the system can use a vacuum container (e.g., a VACUTAINER™).

It is important to note that, in this embodiment, it is important that the vacuum container (e.g., the VACUTAINER™) remain closed/sealed (e.g., with the closure contained on the VACUTAINER™) as the plasma is transferred from the separation device 210 to the storage container 240. When the transfer of plasma to the plasma container 240 is complete, the vacuum container (e.g., the VACUTAINER™) may be accessed (e.g., a feature on the cap 100 may puncture a cover on the vacuum container) to cause plasma contained within the container 240 to flow through line 230 and into the vacuum container.

Figure 8A:
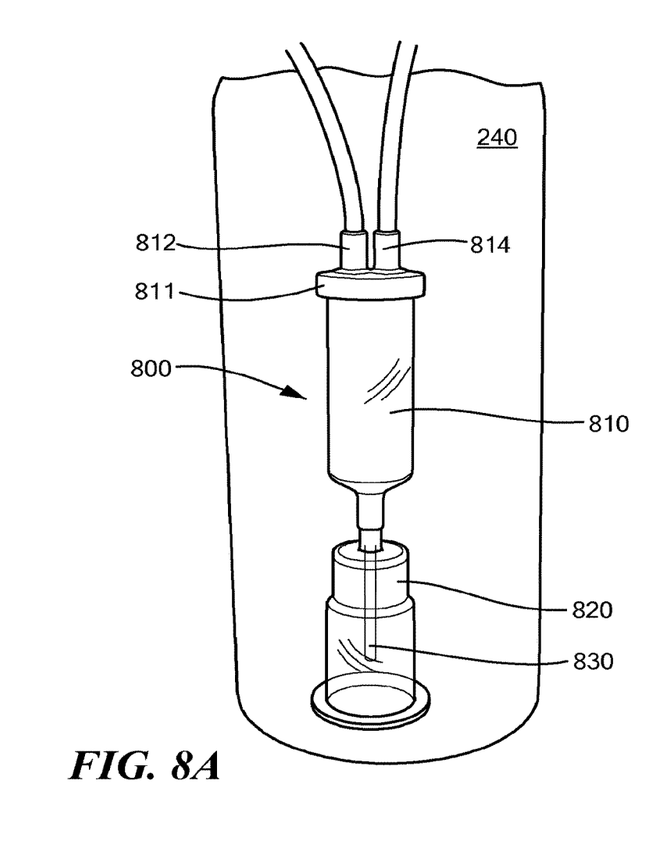
FIGS. 8A and 8B show an alternative sampling system, in accordance with further embodiments of the present invention.
Figure 8B:
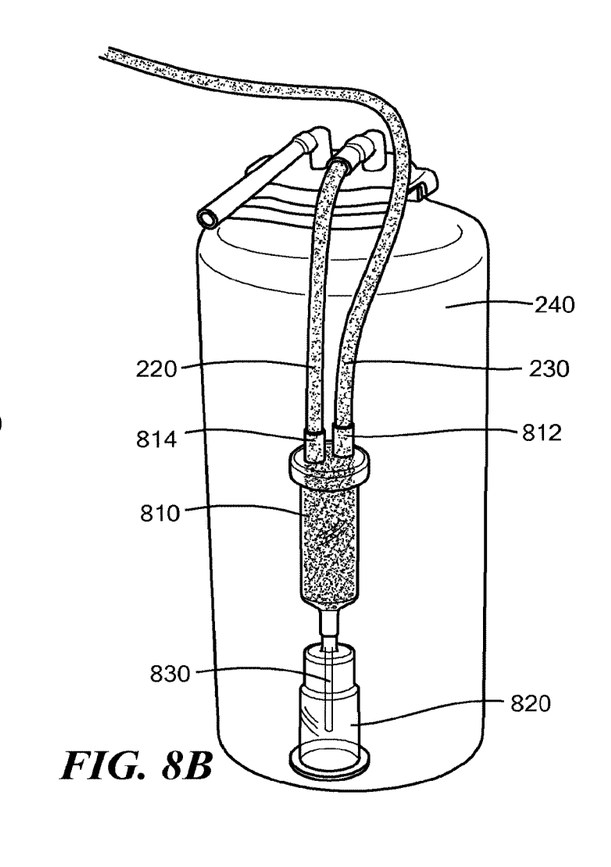

FIGS. 8A and 8B show an alternative embodiment of a sample collection system utilizing a vacuum container (e.g., a VACUTAINER™). In this embodiment, the system 800 includes a collection chamber 810 that collects a volume of the fluid passing through the line (e.g., through lines 220 and 230 fluidly connecting the separation device 210 and the plasma container 240). Like the embodiments discussed above, the collection chamber 810 may have a cap 811 with an inlet 812 for receiving fluid flowing through the lines and outlet 814 through which fluid can leave the container 810. As fluid flows from the separation device 210 to the plasma container 230, the fluid will enter the collection chamber 810, mix with fluid within the chamber 810, and a portion of the fluid (e.g., a portion of the mixed fluid and/or a portion of the fluid entering the chamber 810) will exit the chamber via the outlet 814.

In order to access the fluid within the chamber 810, the system 800 may also include an adapter 820 (e.g., a vacuum container/VACUTAINER™ adapter). To that end, once the fluid collection process is complete (e.g., once the plasma from the separation device 210 is transferred to the plasma container 240 and a sample is collected within the chamber 810), a vacuum container (e.g., a VACUTAINER™) may be connected to the adapter 820. A needle 830 (or similar piercing device) located within the adapter 820 will pierce the closure on the vacuum container and cause the fluid within the chamber 810 to flow into the vacuum container. The vacuum container may then be removed/disconnected from the adapter 820 so that the collected sample may be processed and/or tested.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A flow through fluid sampling system comprising:
   a sample tube configured to collect a sample of a fluid and having an open top; and
   a cap having a body portion and configured to be secured to the sample tube to close the open top, the cap including:
      an inflow port extending through the body portion and configured to allow fluid to enter the fluid sample tube; and
      an outflow port extending through the body portion and configured to allow fluid to leave the sample tube as fluid enters the sample tube via the inflow port.

2. A flow through sampling system according to claim 1, wherein the inflow port is configured to be fluidly connected to a blood separation device of a plasmapheresis system.

3. A flow through sampling system according to claim 2, wherein the inflow port is configured to be fluidly connected to an outlet of the blood separation device.

4. A flow through sampling system according to claim 2, wherein the outflow port is configured to be fluidly connected to a plasma storage bottle.

5. A flow through sampling system according to claim 1, further comprising an occluder located within the cap, the occluder impinging the flow of fluid from the inflow port, thereby reducing mixing within the sample tube.

6. A flow through sampling system according to claim 1, wherein the cap further includes a chamber having a bottom wall, the chamber located between the inflow port and the sample tube.

7. A flow through sampling system according to claim 6, wherein the bottom wall includes a flow path extending therethrough, the chamber and the sample tube in fluid communication via the flow path.

8. A flow through sampling system according to claim 6, further comprising a vent channel extending through the cap, the vent channel configured to allow air from the sample tube to vent through the vent channel.

9. A flow through sampling system according to claim 8, wherein the vent channel includes a bacteriostatic filter.

10. A flow through sampling system according to claim 9, wherein the bacteriostatic filter is configured to stop air flow through the bacteriostatic filter when wet.

11. A method for collecting a sample of fluid comprising:
   connecting a flow through fluid sampling system to a line through which a fluid flows, the fluid sampling system including:
      a sample tube configured to collect a sample of a fluid and having an open top; and
      a cap having a body portion and configured to be secured to the sample tube to close the open top, the cap including:
         an inflow port extending through the body portion and configured to allow fluid to enter the fluid sample tube from the line; and
         an outflow port extending through the body portion and configured to allow fluid to exit the sample tube and re-enter the line as fluid enters the sample tube via the inflow port;
   flowing fluid through the line, at least a portion of the fluid flowing through the line entering the sample tube through the inflow port.

12. A method according to claim 11, wherein additional fluid entering the sample tube mixes with fluid already collected within the sample tube.

13. A method according to claim 11, wherein at least a portion of the fluid entering the sample tube exits the sample tube through the outflow port.

14. A method according to claim 11, further comprising fluidly connecting the inflow port to a blood separation device of a plasmapheresis system.

15. A method according to claim 14, further comprising fluidly connecting the inflow port to an outlet of the blood separation device.

16. A method according to claim 14, further comprising fluidly connecting the outflow port to a plasma storage bottle.

17. A method according to claim 11, wherein the cap further includes an occluder, the occluder impinging the flow of fluid from the inflow port, thereby reducing mixing within the sample tube.

18. A method according to claim 11, wherein the fluid sampling system further includes a chamber within the cap, the chamber having a bottom wall and located between the inflow port and the sample tube.

19. A method according to claim 18, wherein the bottom wall includes a flow path extending therethrough, the chamber and the sample tube in fluid communication via the flow path.

20. A method according to claim 18, wherein the fluid sampling port includes a vent channel extending through the cap, air from the sample tube being vented through the vent channel as fluid enters the sample tube.

21. A method according to claim 20, wherein the vent channel includes a bacteriostatic filter.

22. A method according to claim 21, wherein the bacteriostatic filter is configured to stop air flow through the bacteriostatic filter when wet.

* * * * *